US00PP20182P2

(12) United States Plant Patent
Bacon

(10) Patent No.: US PP20,182 P2
(45) Date of Patent: Jul. 21, 2009

(54) PEACH TREE NAMED 'SUPECHSITEEN'

(50) Latin Name: *Prunus persica*
Varietal Denomination: Supechsixteen

(75) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/155,000

(22) Filed: May 28, 2008

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP13,177 P2 * 11/2002 Mowrey et al.

* cited by examiner

*Primary Examiner*—Kent L Bell
(74) *Attorney, Agent, or Firm*—Knobbe, Martens, Olson & Bear LLP

(57) ABSTRACT

A new and distinct peach tree variety, *Prunus persica,* cv. 'Supechsixteen' is characterized by low chilling requirement (about 200 hours at or below 7.2° C.), early harvest (May 8 near Wasco, Kern County, Calif.), approximately 90–100% red over-color, bright yellow background color and flesh color, excellent eating quality with crisp-juicy non-melting texture and relatively high soluble solids (13% brix) for an early-season peach.

1 Drawing Sheet

Latin name of the genus and species claimed: *Prunus persica.*
Variety denomination: 'Supechsixteen'.

BACKGROUND AND SUMMARY OF THE INVENTION

This invention relates to the discovery and asexual propagation of a new and distinct variety of peach, *Prunus persica* cv. 'Supechsixteen'. The new variety was first hybridized, selected, and evaluated as breeder number 'PE216' by Terry Bacon on Sun World Experimental Ranch 540 near Mecca, Calif. in Riverside County. The variety originated by hybridization.

The new variety is characterized by a low chilling requirement (about 200 hours at or below 7.2° C.), early harvest (May 8 near Wasco, Kern County, Calif.), approximately 90–100% red over-color, bright yellow background color and flesh color, excellent eating quality with crisp-juicy non-melting texture and relatively high soluble solids (13% brix) for an early-season peach.

The seed parent is '94003-024-230', an unpatented Sun World breeding selection, and the pollen parent is an unknown Sun World breeding selection. The new variety was produced as a result of open pollination in 2001. The date of planting of the new variety was January 2002, and the date of first flowering was February 2003. The new peach variety was first asexually propagated by Terry Bacon near Wasco, Kern County, Calif. in 2004 by budding onto 'Nemared' (unpatented) rootstock.

The new variety is distinguished from its seed parent, '94003-024-230', in that it ripens 3 days later than the seed parent and has approximately 90–100% red over-color and bright yellow background color, while the seed parent has only approximately 50% over-color and a green background color.

The new variety most closely resembles the commercial low chill peach 'Supechfifteen' (U.S. Plant Pat. No. 13,177), but may be distinguished from 'Supechfifteen' in that the new variety ripens 3 days later, has approximately 90–100% red over-color, non-melting flesh, and 13% soluble solids (brix), while 'Supechfifteen' has approximately 60% red over-color, melting flesh, and 12% brix.

The new variety has been shown to maintain its distinguishing characteristics through successive asexual propagations by, for example, budding onto 'Nemared' rootstock.

BRIEF DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon the R.H.S. Colour Chart published by The Royal Horticultural Society, London, England.

The descriptive matter which follows pertains to 3 year old 'Supechsixteen' plants on Nemared rootstock, grown in the vicinity of Wasco, Kern County, Calif., during 2007 and is believed to apply to plants of the variety grown under similar conditions of soil and climate elsewhere.

TREE

General: (Measurements taken on 3 year old trees grown in the Sun World Breeding Program germplasm block near Wasco, Calif. unless otherwise noted.)

*Size.*—Medium. Normal for most peach varieties. Reaches a height of approximately 3.2 meters including normal pruning.

*Vigor.*—Vigorous; growth of approximately 1.8 to 2 meters in height during the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Self-fertile.

*Canopy density.*—Dense. Pruning is required to open tree vase shape, allowing more sunlight to center of tree.

*Hardiness.*—Hardy in all fruit growing areas of California. Winter chilling requirement is approximately 200 hours at or below approximately 7.2° C.

*Disease resistance/susceptibility.*—No specific testing for relative plant disease resistance/susceptibility has been designed. Under close observation in the area described in Description of Variety, no particular plant/fruit disease resistance/susceptibility has been observed.

Trunk: (Measurements at approximately 30 cm above soil line).

*Diameter.*—Approximately 22 cm, varies with soil type, fertility, climatic conditions and cultural practices.

*Texture.*—Medium shaggy, increases with age of tree.

*Trunk color.*—About Light Greyed-green 198D to Dark Greyed-red 178A, becomes darker with age.

Branches: (Measurements at approximately 90 cm above soil line).

*Size.*—Diameter ranged from approximately 8 to approximately 10 cm.

*Texture.*—Smooth on first year wood, increasing roughness with tree age.

*Color.*—Branches vary from about Dark Greyed-orange 166A to Light Greyed-green 198D.

*Lenticels.*—Numerous. Color: About Light Greyed-orange 164C. Length: Approximately 2 mm. Width: Approximately 0.5 mm.

Flowering shoots: (Data taken in July at midpoint of current-season growth).

*Size.*—Average diameter approximately 5 mm.

*Color.*—Topside: About Dark Red-purple 59A. Underside: About Medium Yellow-green 146D.

*Flowering shoot lenticels.*—None Observed.

*Flowering shoot leaf buds.*—Shape: Elliptic. Width: Approximately 1.5 mm. Length: Approximately 4 mm. Color: About Light Greyed-green 196A.

*Flowering shoot flower buds.*—Shape: Obovate. Width: Approximately 2 mm. Length: Approximately 4 mm. Color: About Medium Grey 201B. Number per node: Usually 2.

FOLIAGE

Leaves: (Data taken in July on fully expanded leaf at midpoint of current-season growth.)

*Size.*—Average length: Approximately 165 mm. Average width: Approximately 32 mm.

*Thickness.*—Medium.

*Color.*—Upper surface: About Medium Green 137C. Lower surface: About Medium Yellow-green 146C.

*Form.*—Lanceolate.

*Tip.*—Acuminate.

*Base.*—Acuminate.

*Margin.*—Finely crenate.

*Venation.*—Pinnately net veined.

*Surface texture.*—Smooth.

Petiole:

*Average length.*—Approximately 10 mm.

*Average diameter.*—Approximately 2 mm.

*Color.*—About Light Yellow-green 147C.

Leaf stipules:

*Number.*—None observed.

Leaf glands:

*Form.*—Globose.

*Number.*—Varies from 2 to 4.

*Position.*—Alternate on upper portion of petiole and base of leaf blade.

*Average size.*—Approximately 1 mm by approximately 1 mm.

*Color.*—About Dark Greyed-red 178A.

FLOWERS: (FULLY OPENED)

General:

Flower blooming period:

*First bloom.*—Approximately Feb. 10, 2007.

*Full bloom.*—Approximately Feb. 15, 2007.

Type: Non-showy.

Size:

*Average diameter.*—Approximately 24–30 mm.

*Flower aroma.*—Very slight.

Peduncle:

*Length.*—Approximately 3 mm to approximately 4 mm.

*Diameter.*—Approximately 2 mm.

*Color.*—About Medium Yellow-green 146C.

Petals:

*Number.*—5.

*Arrangement.*—Free.

*Length.*—Approximately 13 mm to approximately 15 mm.

*Diameter.*—Approximately 8 mm to approximately 11 mm.

*Shape.*—Broadly ovate.

*Apex shape.*—Rounded.

*Base shape.*—Narrows at point of attachment.

*Color.*—About Medium Red-purple 63A when newly opened, darkening with advanced senescence.

*Surface texture.*—Smooth.

*Margins.*—Smooth.

Sepals:

*Number.*—5.

*Length.*—Approximately 5 mm.

*Diameter.*—Approximately 4 mm.

*Shape.*—Ovate.

*Color.*—About Dark Greyed-red 178A.

*Surface texture.*—Smooth.

Stamens:

*Number.*—Ranges from approximately 30 to approximately 40, average 38.

*Average length.*—Approximately 13 mm.

*Filament color.*—About Light Red-purple 62D.

*Anther color.*—About Medium Greyed-red 179A.
*Flower pollen color.*—About Medium Yellow-orange 17B.

Pistil:
*Number.*—Usually one, occasionally two.
*Average length.*—Approximately 16 mm to approximately 19 mm.
*Ovary diameter.*—Approximately 3 mm.
*Pubescence.*—Slight.
*Stigma extension in comparison to anthers.*—Slightly above anthers.

FRUIT

General: (Data taken at firm-ripe on mature tree managed to obtain maximum quality under conditions stated in Description of Variety.)
*Harvest.*—Date of first pick: Approximately May 5, 2007. Date of last pick: Approximately May 14, 2007.

Size:
*Length* (*stem end to apex*).—Approximately 66 mm.
*Diameter in line with suture plane.*—Approximately 68 mm.
*Diameter perpendicular to suture plane.*—Approximately 69 mm.
*Average weight.*—Approximately 165 gm.

Form:
*Viewed from apex.*—Round, nearly symmetrical.
*Viewed from side, facing suture.*—Round, nearly symmetrical.
*Viewed from side, perpendicular to suture.*—Round, nearly symmetrical.

Apex shape: Flat.

Fruit stem-end cavity depth: Deep.

Fruit stem:
*Length.*—Approximately 8 mm.
*Diameter.*—Approximately 2.5 mm.
*Color.*—About Green 164B.

Fruit skin:
*Thickness.*—Medium.
*Adherence to flesh.*—Tenacious.
*Surface texture.*—Smooth.
*Pubescence.*—Short and slight.
*Bloom.*—None.
*Ground color.*—About Yellow 11A with slight green background when mature.
*Overcolor.*—About Red 45D to 59C when mature, covering approximately 90–100% of fruit surface.
*Taste.*—Neutral.

Flesh:
*Ripens.*—Evenly.
*Texture.*—Firm, fine.
*Fibers.*—Few, short.
*Flavor.*—Sweet-mild.
*Brix.*—Approximately 13%.
*Juice.*—Moderate.
*Aroma.*—Slight.
*Color.*—About Yellow 17C, sometimes slight Green 145B near stone.

Fruit use: Dessert. Market, local and long distance.

Fruit shipping and keeping quality: Good, holds well in cold storage for approximately 4 weeks and maintains good firmness and eating quality, minimal bruising and scarring in packing and shipping trials.

Stone: (Measurements taken on dried stones.)
*Stone freeness.*—Clingstone.
*Stone size.*—Length: Approximately 40 mm. Diameter in line with suture plane: Approximately 30 mm. Diameter perpendicular to suture plane: Approximately 20 mm.
*Stone form.*—Viewed from side: Elliptical oblong, nearly symmetrical. Viewed from stem end: Oval, nearly symmetrical.
*Stone shape.*—Base shape: Rounded and retuse at stem attachment. Apex shape: Rounded with a small, sharp point.
*Stone surface.*—Heavily ridged throughout.
*Stone halves.*—Nearly equal.
*Stone ridges.*—About 1 on each side of the suture, pronounced, beginning at the base and extending throughout the length of the stone.
*Stone outgrowing keel.*—Partially developed.
*Stone tendency to split.*—Slight.
*Stone color.*—About Light Greyed-orange 164C to 164D when dried.

What is claimed is:

1. A new and distinct peach tree as herein described and illustrated.

* * * * *

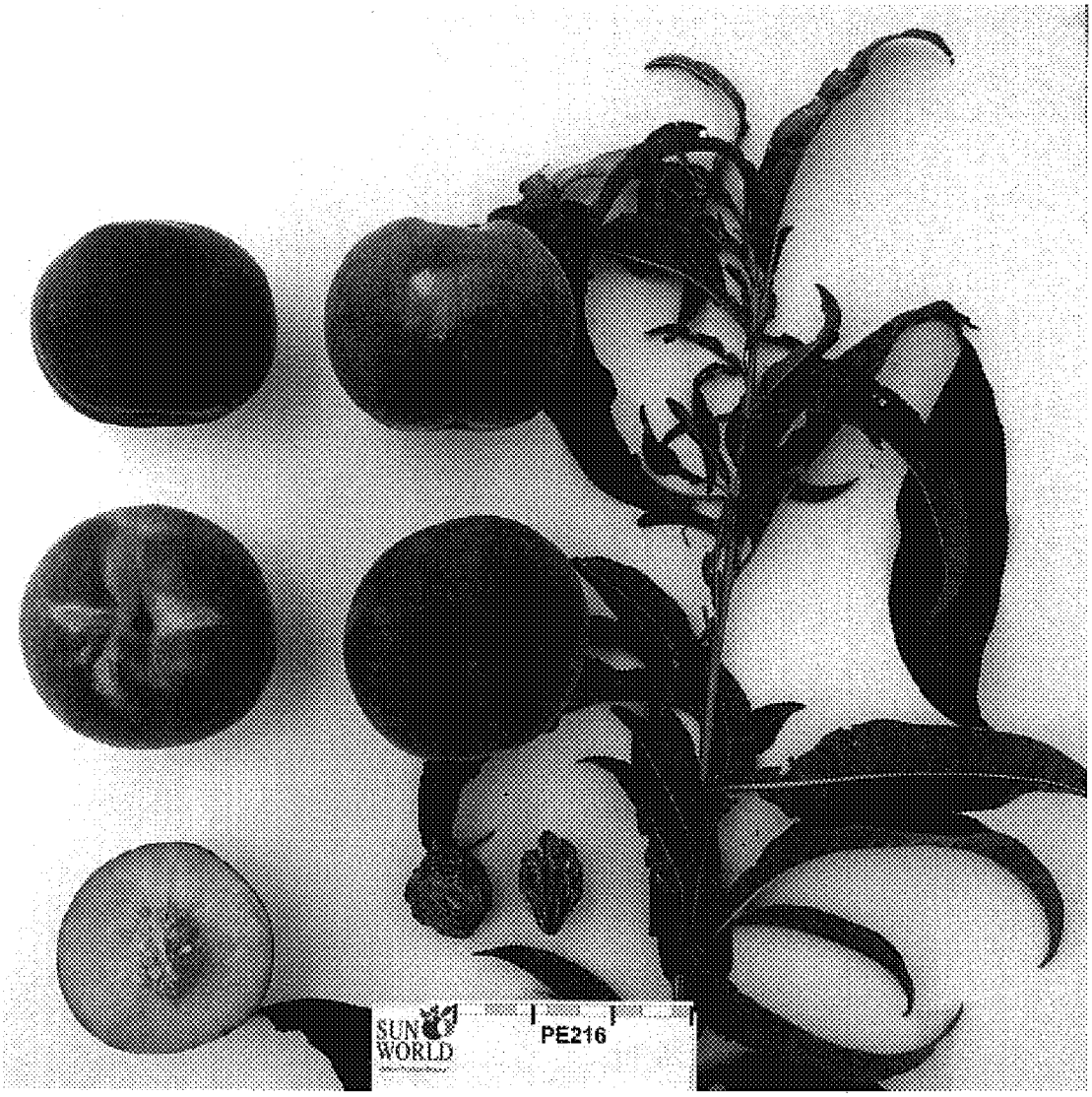
SUN WORLD
PE216

UNITED STATES PATENT AND TRADEMARK OFFICE

CERTIFICATE OF CORRECTION

PATENT NO. : PP 20,182 P2
APPLICATION NO. : 12/155000
DATED : July 21, 2009
INVENTOR(S) : Terry Bacon It is certified that error appears in the above-identified patent and that said Letters Patent is hereby corrected as shown below:

Cover page, item [54] and col. 1, the title should be changed from "PEACH TREE NAMED 'SUPECHSITEEN'" to --PEACH TREE NAMED 'SUPECHSIXTEEN'--.

Signed and Sealed this

Twenty-second Day of December, 2009

David J. Kappos

David J. Kappos
*Director of the United States Patent and Trademark Office*